US006521778B1

(12) United States Patent
Fischer et al.

(10) Patent No.: US 6,521,778 B1
(45) Date of Patent: Feb. 18, 2003

(54) CATALYST COMPRISING A COMPLEX OF A METAL FROM SUBGROUP VIII BASED ON A BIDENTATE PHOSPHONITE LIGAND, AND METHOD FOR PRODUCING NITRILES

(75) Inventors: Jakob Fischer, Kirchdorf (DE); Wolfgang Siegel, Limburgerhof (DE); Dagmar Pascale Keitel, Limburgerhof (DE); Lorenz Siggel, Heidelberg (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/701,601

(22) PCT Filed: Jun. 4, 1999

(86) PCT No.: PCT/EP99/03888

§ 371 (c)(1),
(2), (4) Date: Nov. 30, 2000

(87) PCT Pub. No.: WO99/64155

PCT Pub. Date: Dec. 16, 1999

(30) Foreign Application Priority Data

Jun. 5, 1998 (DE) .......................... 198 25 212

(51) Int. Cl.[7] .................... C01C 253/00; B01J 27/185
(52) U.S. Cl. ................. 558/338; 502/213; 558/339; 558/340; 558/156
(58) Field of Search .................... 502/213; 558/338, 558/339, 340, 156

(56) References Cited

U.S. PATENT DOCUMENTS

| | | | |
|---|---|---|---|
| 3,766,237 A | 10/1973 | Chia et al. ............... | 260/465 |
| 4,652,542 A | 3/1987 | Duggan et al. ........... | 502/154 |
| 4,663,489 A | 5/1987 | Duggan et al. ........... | 568/678 |
| 4,692,426 A | 9/1987 | Duggan et al. ........... | 502/154 |
| 5,360,938 A | 11/1994 | Babin et al. ............. | 568/449 |
| 5,440,067 A | 8/1995 | Druliner ................. | 558/335 |
| 5,449,807 A | 9/1995 | Druliner ................. | 558/338 |
| 5,512,695 A | 4/1996 | Kreutzer et al. ......... | 558/338 |
| 5,523,453 A | 6/1996 | Breikss ................. | 558/338 |
| 5,600,032 A | 2/1997 | Sato et al. .............. | 568/903 |
| 5,696,280 A | 12/1997 | Shapiro ................. | 558/140 |
| 5,712,403 A | 1/1998 | Sato et al. .............. | 556/19 |
| 5,821,378 A | 10/1998 | Foo et al. ............... | 558/338 |
| 6,242,633 B1 * | 6/2001 | Fischer et al. .......... | 558/334 |

FOREIGN PATENT DOCUMENTS

| | | |
|---|---|---|
| CA | 2303776 | 3/1999 |
| WO | WO 95/14659 | 6/1995 |
| WO | WO 96/11182 | 4/1996 |
| WO | WO 96/22968 | 8/1996 |
| WO | WO 96/33969 | 10/1996 |
| WO | WO 97/23446 | 7/1997 |
| WO | WO 97/36856 | 10/1997 |
| WO | WO 98/43935 | 10/1998 |
| WO | WO 99/13983 | 3/1999 |
| WO | WO 99/46044 | 9/1999 |

OTHER PUBLICATIONS

Baker et al. "Chiral Aryl Diphosphites: a New Class of Ligands for Hydrocyanation Catalysts" J. Chem. Soc. Chem Commun. (1991) pp. 1292–1293.

Baker et al. "Chelating Diphosphite Complexes of Nickel (O) and Platinum (O): Their Remarkable Stability and Hydrocyanation Activity" J. Am. Chem. Soc. Chem. Commum. (1991) pp. 803–804.

"Applied Homogenous Catalysis with Organometallic Compounds" vol. 1 (1996) pp. 465–486.

Weissermal et al. "Industrielle Organische Chemie" 4th Ed. (1994) pp. 266–270.

\* cited by examiner

*Primary Examiner*—Joseph K. McKane
*Assistant Examiner*—Rebecca Anderson
(74) *Attorney, Agent, or Firm*—Keil & Weinkauf

(57) ABSTRACT

A catalyst which comprises at least one complex of a metal of subgroup VIII having at least one bidentate phosphonite ligand of the formula I

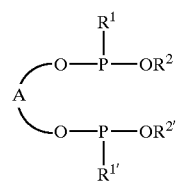

or salts and mixtures thereof, a process for the preparation of mixtures of monoolefinic $C_5$-mononitriles, a process for the catalytic isomerization of branched aliphatic monoalkenenitriles and a process for the preparation of adiponitrile.

14 Claims, No Drawings

CATALYST COMPRISING A COMPLEX OF A METAL FROM SUBGROUP VIII BASED ON A BIDENTATE PHOSPHONITE LIGAND, AND METHOD FOR PRODUCING NITRILES

This a 371 of PCT/EP99/03888 with international filing date of Jun. 4, 1999.

The present invention relates to a catalyst which comprises a complex of a metal of subgroup VIII, which comprises at least one bidentate phosphonite ligand, a process for the preparation of mixtures of monoolefinic $C_5$-mononitriles and a process for the preparation of adipodinitrile by catalytic hydrocyanation in the presence of such a catalyst.

For the industrial production of polyamides, there is a considerable demand worldwide for α,ω-alkylenediamines, which serve as an important starting material. α,ω-alkylenediamines, such as hexamethylenediamine, are obtained virtually exclusively by hydrogenating the corresponding dinitriles. Virtually all industrial routes for the production of hexamethylenediamine are therefore essentially variants of the production of adipodinitrile, of which about 1.0 million metric tons are produced annually worldwide.

K. Weissermel, H.-J. Arpe, Industrielle Organische Chemie, 4th edition, VCH Weinheim, page 266 et seq., describe four basically different routes for the preparation of adipodinitrile, including the direct hydrocyanation of 1,3-butadiene with hydrogen cyanide. In the last-mentioned process, monoaddition in a first stage gives a mixture of isomeric pentenenitriles, which is isomerized in a second stage to give predominantly 3- and 4-pentenenitrile. Adipodinitrile is then formed in a third stage by an anti-Markownikow hydrogen cyanide addition reaction with 4-pentenenitrile.

"Applied Homogeneous Catalysis with Organometalic Compounds", Vol. 1, VCH Weinheim, page 465 et seq., describes in general the addition reaction of hydrogen cyanide with olefins under heterogeneous and homogeneous catalysis. In particular, catalysts based on phosphine, phosphite and phosphinite complexes of nickel and of palladium are used. For the preparation of adipodinitrile by hydrocyanation of butadiene, predominantly nickel(0) phosphite catalysts are used, in the presence or absence of a Lewis acid as a promoter.

J. Chem. Soc., Chem. Commun., 1991, page 1292, describes chiral aryl diphosphites as ligands for hydrocyanation catalysts. In these ligands, the phosphite group is bonded via two of its oxygen atoms to the 3- and 3'-positions of a 2,2'-binaphthyl unit, with which it thus forms a 7-membered heterocycle. In addition, two of these heterocycles may likewise be linked via a 2,2'-binaphthyl unit to form a bidentate chelate ligand. In J. Chem. Soc., Chem. Commun., 1991, page 803 et seq., analogous chelate diphosphite complexes of nickel(0) and platinum(0) are described for this purpose, a 2,2'-biphenyl unit being used instead of a 2,2'-binaphthyl unit as the bridging group.

U.S. Pat. No. 5,449,807 describes a process for the gas-phase hydrocyanation of diolefins in the presence of a supported nickel catalyst based on at least one bidentate phosphite ligand, the two phosphite groups being bridged by an unsubstituted or substituted 2,2'-biphenyl group. U.S. Pat. No. 5,440,067 describes a process for the gas-phase isomerization of 2-alkyl-3-monoalkenenitriles to give linear 3- and/or 4-monoalkenenitriles in the presence of the catalysts described in U.S. Pat. No. 5,449,807.

WO 95/14659 describes a process for the hydrocyanation of monoolefins, in which catalysts based on zero-valent nickel and bidentate phosphite ligands may be used. In these ligands, the phosphite groups together with two of their oxygen atoms are part of an aryl-fused 7-membered heterocycle. Pairs of these phosphite groups are then bridged by aryl-fused alkylene groups via the oxygen atoms which are not part of the heterocycle.

U.S. Pat. No. 5,512,695 likewise describes a process for the hydrocyanation of monoolefins in the presence of a nickel catalyst which comprises a bidentate phosphite ligand.

WO 96/11182 describes a process for hydrocyanation in the presence of a nickel catalyst based on a bidentate or polydentate phosphite ligand in which the phosphite groups are not part of a heterocycle. The groups used for bridging the phosphite groups correspond to those described in WO 95/14659.

U.S. Pat. No. 5,523,453 describes a process for hydrocyanation in the presence of a nickel catalyst based on a bidentate ligand which comprises at least one phosphinite group and a further phosphorus-containing group which is selected from phosphinites and phosphites. The two phosphorus-containing groups of these bidentate ligands are in turn bridged via aryl-fused groups. WO 97/23446 describes a process for the hydrocyanation of diolefins and for the isomerization of 2-alkyl-3-monoalkenenitriles in the presence of catalysts which correspond to those described in U.S. Pat. No. 5,523,453.

WO 96/22968 likewise describes a process for the hydrocyanation of diolefinic compounds and for the isomerization of the resulting, nonconjugated 2-alkyl-3-monoalkenenitriles, a nickel(0) catalyst based on a polydentate phosphite ligand being used in the presence of a Lewis acid as promoter. The phosphite groups of these polydentate ligands are once again components of aryl-fused heterocycles and may be bridged via aryl-fused groups.

None of the abovementioned publications describes hydrocyanation catalysts based on phosphonite ligands. In particular, no catalysts based on bidentate chelate phosphonites are described.

U.S. Pat. No. 3,766,237 describes a process for the hydrocyanation of ethylenically unsaturated compounds which may have further functional groups, such as nitriles, in the presence of a nickel catalyst. These nickel catalysts carry four ligands of the formula M(X,Y,Z), where X, Y and Z, independently of one another, are each a radical R or OR and R is selected from alkyl and aryl groups of up to 18 carbon atoms. However, only phosphines and phosphites are mentioned explicitly and are used in the examples for the hydrocyanation. On the other hand, it is not disclosed that phosphonites can be used as ligands for nickel(0) hydrocyanation catalysts. In particular, no bidentate chelate phosphonite ligands are described.

It is an object of the present invention to provide novel catalysts based on a metal of subgroup VIII. They should preferably have good selectivity and good catalytic activity in the hydrocyanation of 1,3-butadiene and 1,3-butadiene-containing hydrocarbon mixtures. Preferably, they should also be suitable for the catalytic isomerization of monoalkenenitriles and for the addition reaction of the second molecule of hydrogen cyanide with said monoalkenenitriles, for example for the preparation of adipodinitrile.

We have surprisingly found that this object is achieved by catalysts based on a metal of subgroup VIII which comprise at least one bidentate phosphonite ligand.

The present invention therefore relates to a catalyst comprising a complex of a metal of subgroup VIII, having a bidentate phosphonite ligand of the formula I

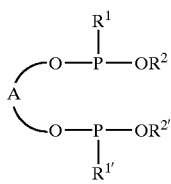

(I)

where

A is a $C_2$- to $C_7$-alkylene bridge which may have 1, 2 or 3 double bonds and/or 1, 2 or 3 substituents which are selected from alkyl, cycloalkyl and aryl, it being possible for the aryl substituent additionally to carry 1, 2 or 3 substituents which are selected from alkyl, alkoxy, halogen, trifluoromethyl, nitro, alkoxycarbonyl and cyano, and/or the $C_2$- to $C_7$-alkylene bridge may be interrupted by 1, 2 or 3 non-neighboring, unsubstituted or substituted heteroatoms, and/or the $C_2$- to $C_7$-alkylene bridge may be fused with one, two or three aryl and/or hetaryl groups, it being possible for the fused aryl and hetaryl groups each to carry 1, 2 or 3 substituents which are selected from alkyl, cycloalkyl, aryl, alkoxy, cycloalkoxy, aryloxy, acyl, halogen, trifluoromethyl, nitro, cyano, carboxyl, alkoxycarbonyl and $NE^1E^2$, where $E^1$ and $E^2$ are identical or different and are each alkyl, cycloalkyl or aryl, $R^1$ and $R^{1'}$, independently of one another, are each alkyl, cycloalkyl, aryl or hetaryl, each of which may carry 1, 2 or 3 substituents which are selected from alkyl, cycloalkyl and aryl, $R^2$ and $R^{2'}$, independently of one another, are each alkyl, cycloalkyl, aryl or hetaryl, it being possible for the aryl and hetaryl groups each to carry 1, 2 or 3 substituents which are selected from alkyl, cycloalkyl, aryl, alkoxy, cycloalkoxy, aryloxy, acyl, halogen, trifluoromethyl, nitro, cyano, carboxyl, alkoxycarbonyl and $NE^1E^2$, where $E^1$ and $E^2$ may have the abovementioned meanings, or a salt or mixture thereof.

In the present invention, the term alkyl includes straight-chain and branched alkyl groups. These are preferably straight-chain or branched $C_1$–$C_8$-alkyl, preferably $C_1$–$C_6$-alkyl, particularly preferably $C_1$–$C_4$-alkyl groups. Examples of alkyl groups are in particular methyl, ethyl, propyl, isopropyl, n-butyl, 2-butyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 2-heptyl, 3-heptyl, 2-ethylpentyl, 1-propylbutyl and octyl.

The cycloalkyl group is preferably $C_5$–$C_7$-cycloalkyl, such as cyclopentyl, cyclohexyl or cycloheptyl.

If the cycloalkyl group is substituted, it preferably has 1, 2, 3, 4 or 5, in particular 1, 2 or 3, substituents selected from alkyl, alkoxy, halogen or trifluoromethyl.

Aryl is preferably phenyl, tolyl, xylyl, mesityl, naphthyl, anthracenyl, phenanthrenyl or naphthacenyl, in particular phenyl or naphthyl. If the aryl group is substituted, it preferably has 1, 2, 3, 4 or 5, particularly preferably 1, 2 or 3, especially 1 or 2, substituents in any position.

Hetaryl is preferably pyridyl, quinolyl, acridinyl, pyridazinyl, pyrimidinyl or pyrazinyl.

Substituted hetaryl radicals preferably have 1, 2 or 3 substituents selected from alkyl, alkoxy, halogen and trifluoromentyl.

The above statements on alkyl, cycloalkyl and aryl radicals are applicable in a corresponding manner to alkoxy, cycloalkoxy and aryloxy radicals.

$NE^1E^2$ is preferably N,N-dimethyl, N,N-diethyl, N,N-dipropyl, N,N-diisopropyl, N,N-di-n-butyl, N,N-di-tert-butyl, N,N-dicyclohexyl or N,N-diphenyl.

Halogen is fluorine, chlorine, bromine or iodine, preferably fluorine or chlorine.

In the phosphonite ligands of the formula I, $R^1$ and $R^2$, and $R^{1'}$ and $R^{2'}$, are not linked to one another.

A is preferably a $C_2$–$C_7$-alkylene bridge which is fused with 1, 2 or 3 aryl groups and which additionally may have a substituent which is selected from alkyl, cycloalkyl and unsubstituted and substituted aryl and/or which additionally may be interrupted by an unsubstituted or substituted heteroarom.

The fused aryls of the radicals A are preferably benzene or naphthalene. Fused benzene rings are preferably unsubstituted or have 1, 2 or 3, in particular 1 or 2, substituents which are selected from alkyl, alkoxy, halogen, trifluoromethyl, nitro, carboxyl, alkoxycarbonyl and cyano. Fused naphthalenes are preferably unsubstituted or have, in the non-fused ring and/or in the fused ring, in each case 1, 2 or 3, in particular 1 or 2, of the substituents mentioned above for the fused benzene rings. Fused naphthalenes which are substituted in the fused ring preferably have a substituent in the ortho position to the phosphonite group. This is then preferably alkyl or alkoxycarbonyl. In the case of the substituents of the fused aryls, alkyl is preferably $C_1$- to $C_4$-alkyl, in particular methyl, isopropyl or tert-butyl. Alkoxy is preferably $C_1$–$C_4$-alkoxy, in particular methoxy. Alkoxycarbonyl is preferably $C_1$- to $C_4$-alkoxycarbonyl. Halogen is in particular fluorine or chlorine.

If the $C_2$- to $C_7$-alkylene bridge of the radical A is interrupted by 1, 2 or 3 unsubstituted or substituted heteroatoms, these are selected from O, S or $NR^5$, where $R^5$ is alkyl, cycloalkyl or aryl. Preferably, the $C_2$- to $C_7$-alkylene bridge of the radical A is interrupted by an unsubstituted or substituted heteroatom.

If the $C_2$- to $C_7$-alkylene bridge of the radical A is substituted, it has 1, 2 or 3 substituents, in particular 1 substituent, which is/are selected from alkyl, cycloalkyl and aryl, it being possible for the aryl substituent additionally to carry 1, 2 or 3 substituents which are selected from alkyl, alkoxy, halogen, trifluoromethyl, nitro, alkoxycarbonyl and cyano. Preferably, the alkylene bridge A has one substituent which is selected from methyl, ethyl, isopropyl, phenyl or p-($C_1$- to $C_4$-alkyl)phenyl, preferably p-methylphenyl or p-($C_1$- to $C_4$-alkoxy)phenyl, preferably p-methoxyphenyl, p-halophenyl, preferably p-chlorophenyl, and p-trifluoromethylphenyl.

Preferably, A is a $C_4$- to $C_7$-alkylene bridge which is fused and/or substituted and/or interrupted by unsubstituted or substituted heteroatoms, as described above. In particular, A is a $C_4$- to $C_5$-alkylene bridge which is fused with one or two phenyl and/or naphthyl groups, it being possible for the phenyl or naphthyl groups to carry 1, 2 or 3, in particular 1 or 2, of the abovementioned substituents.

In particular, A is a radical of the formulae II.1 to II.5

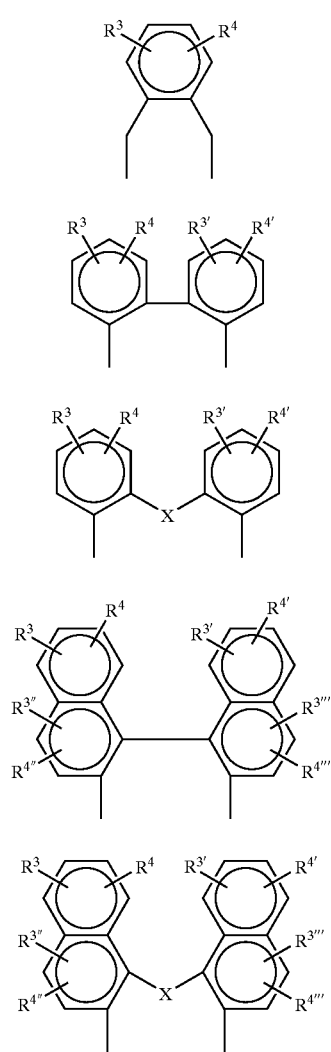

where

X is O, S or NR$^5$, where
R$^5$ is alkyl, cycloalkyl or aryl,
or X is a C$_1$- to C$_3$-alkylene bridge which may have a double bond and/or an alkyl, cycloalkyl or aryl substituent, it being possible for the aryl substituent to carry 1, 2 or 3 substituents, which are selected from alkyl, alkoxy, halogen, trifluoromethyl, nitro, alkoxycarbonyl and cyano,
or X is a C$_2$- or C$_3$-alkylene bridge which is interrupted by O, S or NR$^5$, and R$^3$, R$^{3'}$, R$^{3''}$, R$^{3'''}$, R$^4$, R$^{4'}$, R$^{4''}$ and R$^{4'''}$, independently of one another, are each hydrogen, alkyl, alkoxy, halogen, trifluormethyl, nitro, alkoxycarbonyl or cyano.

Preferably, A is a radical of the formula II.1, where R$^3$ and R$^4$ are each hydrogen.

Preferably, A is a radical of the formula II.2a

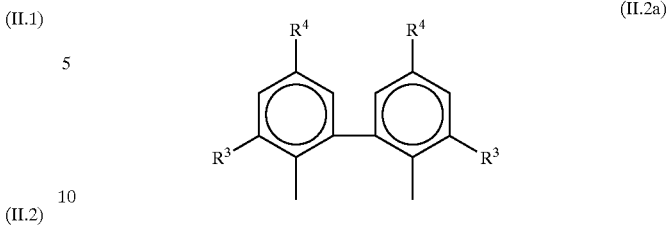

where

R$^3$ is hydrogen or C$_1$- to C$_4$-alkyl, preferably methyl, isopropyl or tert-butyl, and R$^4$ is hydrogen, C$_1$- to C$_4$-alkyl, preferably methyl, isopropyl or tert-butyl, C$_1$- to C$_4$-alkoxy, preferably methoxy, fluorine, chlorine or trifluoromethyl.

Preferably, A is a radical of the formula II.3a

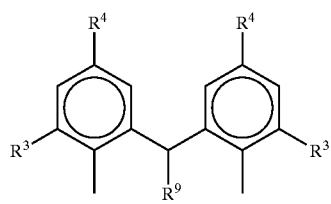

where

R$^3$ and R$^4$ have the meanings mentioned above in the case of the formula II.2a and R$^9$ is hydrogen, C$_1$- to C$_4$-alkyl, preferably methyl or ethyl, phenyl, p-(C$_1$- to C$_4$-alkoxy)phenyl, preferably p-methoxyphenyl, p-fluorophenyl, p-chlorophenyl or p-(trifluoromethyl)phenyl.

Preferably, A is a radical of the formula II.4, where R$^3$, R$^{3'}$, R$^{3''}$, R$^{3'''}$, R$^4$, R$^{4'}$, R$^{4''}$ and R$^{4'''}$ are each hydrogen.

Preferably, A is a radical of the formula II.4, where R$^3$, R$^{3'}$, R$^4$, R$^{4'}$, R$^{4''}$ and R$^{4'''}$ are each hydrogen and R$^{3''}$ and R$^{3'''}$, independently of one another, are each alkoxycarbonyl, preferably methoxycarbonyl, ethoxycarbonyl, n-propoxycarbonyl or isopropoxycarbonyl. In particular, R$^{3''}$ and R$^{3'''}$ are ortho to the phosphonite group.

Preferably, A is a radical of the formula II.5, where R$^3$, R$^{3'}$, R$^{3''}$, R$^{3'''}$, R$^4$, R$^{4'}$, R$^{4''}$ and R$^{4'''}$ are each hydrogen and X is CR$^9$, where R$^9$ has the abovementioned meanings.

Preferably, A is a radical of the formula II.5, where R$^3$, R$^{3'}$, R$^4$, R$^{4'}$, R$^{4''}$ and R$^{4'''}$ are each hydrogen, X is CR$^9$ and R$^{3''}$ and R$^{3'''}$, independently of one another, are each alkoxycarbonyl, preferably methoxycarbonyl, ethoxycarbonyl, n-propoxycarbonyl or isopropoxycarbonyl. In particular, R$^{3''}$ and R$^{3'''}$ are ortho to the phosphonite group.

In the formula I, R$^1$ and R$^{1'}$, independently of one another, are preferably alkyl or aryl, in particular phenyl, 1-naphthyl or 2-naphthyl.

Preferably, R$^2$ and R$^{2'}$, independently of one another, are each phenyl which may carry 1 or 2 substituents which are selected from alkyl, alkoxy, halogen, trifluoromethyl, nitro, cyano, alkoxycarbonyl or carboxyl.

In a preferred embodiment, the phosphonite ligand of the formula I is selected from ligands of the formulae Ia to Ic

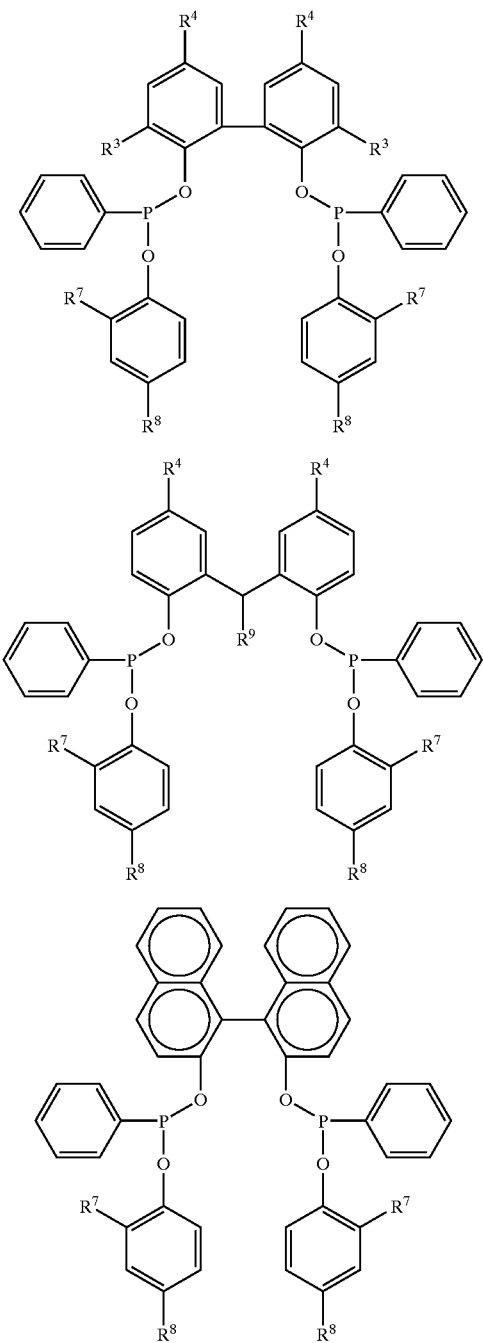

(Ia)

(Ib)

(Ic)

where in the formula Ia $R^3$, $R^4$, $R^7$ and $R^8$ have the following meanings:

| $R^3$ | $R^4$ | $R^7$ | $R^8$ |
|---|---|---|---|
| H | H | H | H |
| tert-butyl | methyl | H | H |
| tert-butyl | methoxy | H | H |
| H | H | methyl | H |
| H | H | ethyl | H |
| H | H | isopropyl | H |
| H | H | tert-butyl | H |

-continued

| $R^3$ | $R^4$ | $R^7$ | $R^8$ |
|---|---|---|---|
| H | Cl | H | H |
| H | $CF_3$ | H | H |
| H | H | methyl | methoxy | in the formula Ib $R^4$, $R^7$, $R^8$ and $R^9$ have the following meanings:

| $R^4$ | $R^7$ | $R^8$ | $R^9$ |
|---|---|---|---|
| H | H | H | H |
| Cl | H | H | H |
| methoxy | H | H | H |
| H | H | H | phenyl |
| H | methyl | H | H |
| H | methyl | methoxy | H |
| H | methyl | methoxy | phenyl | in the formula Ic $R^7$ and $R^8$ have the following meanings:

| $R^7$ | $R^8$ |
|---|---|
| H | H |
| methyl | H |
| ethyl | H |
| isopropyl | H |
| tert-butyl | H |
| methyl | methoxy |
| isopropyl | H |
| isopropyl | methoxy |
| H | Cl |
| H | $CF_3$ |

The present invention furthermore relates to phosphonite ligands of the formula I

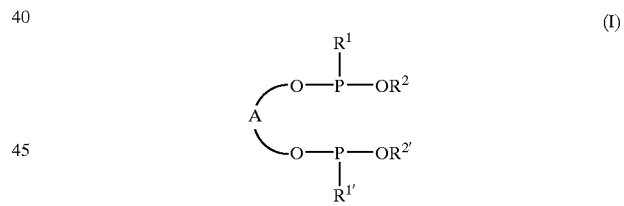

(I)

as defined above, where $R^2$ and $R^{2'}$, independently of one another, are each alkyl, cycloalkyl, aryl or hetaryl, it being possible for the aryl and hetaryl groups each to carry 1 or 2 substituents which are selected from alkyl, cycloalkyl, aryl, alkoxy, cycloalkoxy, aryloxy, acyl, halogen, trifluoromethyl, nitro, cyano, carboxyl, alkoxycarbonyl and $NE^1E^{2'}$ where $E^1$ and $E^2$ may be identical or different and are each alkyl, cycloalkyl or aryl.

$R^2$ and $R^{2'}$, independently of one another, are preferably each phenyl which may carry 1 or 2 of the abovementioned substituents.

The novel catalysts may have one or more of the phosphonite ligands of the formula I. In addition to the ligands of formula I which are described above, they may also have at least one further ligand which is selected from cyanide, halides, amines, carboxylates, acetylacetone, arylsulfonates, alkanesulfonates, hydride, CO, olefins, dienes, cycloolefins, nitrites, N-containing heterocycles, aromatics and heteroaromatics, ethers, $PF_3$ and mono-, bi- and polydentate phosphine, phosphinite, phosphonite and phosphite ligands. These further ligands may likewise be mono-, bi- or polydentate and may have coordinate bonds to the metal of subgroup VIII. Suitable further phosphorus-containing ligands are, for example, the phosphine, phosphinite and phosphite ligands described above as prior art.

Preferably, the metal of subgroup VIII is cobalt, rhodium, ruthenium, palladium or nickel. If the novel catalysts are used for hydrocyanation, the metal of subgroup VIII is in particular nickel.

For the preparation of the phosphonite ligands of the formula I which are used in the novel catalysts, a dihalophosphorus(III) compound III, where $R^1$ (or $R^{1'}$) has the abovementioned meanings, can first be reacted with a monoalcohol IV, where $R^2$ (or $R^{2'}$) has the abovementioned meanings, to give a compound of the formula V, according to the following scheme. If desired, this compound V can be isolated and/or purified by known methods, e.g. by distillation, before the further reaction. The compound V is then reacted with a diol of the formula VI to give the bidentate phosphonite ligands of the formula (I). Where, in the formula (I), $R^1$ is identical to $R_{1'}$ and $R^2$ is identical to $R^{2'}$, two equivalents of the formula V can be reacted with one equivalent of the formula VI in a one-stage reaction. Otherwise, first one equivalent of the formula V is reacted with one equivalent of the formula VI and, after formation of the monocondensate, a second compound of the formula (V) $Cl-PR^{1'}—OR^{2'}$ is added and is further reacted to give the phosphonite of the formula (I).

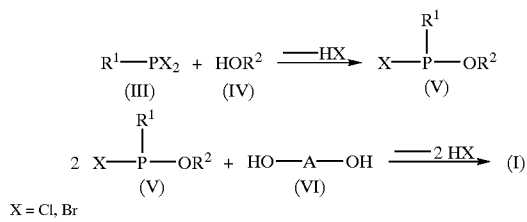

X = Cl, Br

The compound of the formula (III) is preferably a dichlorophosphorus(III) compound. Suitable compounds having the abovementioned radicals $R^1$ are known. If, for example, $R^1$ is phenyl, the compound is dichlorophenylphosphine.

Suitable alcohols of the formula IV, where $R^2$ has the abovementioned meanings, are likewise known. Suitable aromatic alcohols of the formula $HOR^2$ are, for example, 2-tert-butyl-4-methylphenol, 2-isopropylphenol, 2-tert-butylphenol, 4-tert-butylphenol, 2,6-di-tert-butyl-4-methylphenol, 2,4-di-tert-butylphenol, 2,6-di-tert-butylphenol, 2,4-dimethylphenol, 2,5-dimethylphenol, 2,6-dimethylphenol, 3,4-dimethylphenol, 3,5-dimethylphenol, 2-ethylphenol, 3-ethylphenol, 4-ethylphenol, 5-isopropyl-2-methylphenol, m-cresol, o-cresol, p-cresol, 1-naphthol, 2-naphthol, phenol, 1-bromo-2-naphthol, 3-bromophenol, 5-chloroquin-8-ol, 4-chloro-3,5-dimethylphenol, 2-chloro-5-methylphenol, 4-chloro-3-methylphenol, 2-chloro-6-nitrophenol, 2-chlorophenol, 3-chlorophenol, 4-chlorophenol, 4-chlororesorcinol, 2,3-dichlorophenol, 2,4-dichlorophenol, 2,5-dichlorophenol, 2,6-dichlorophenol, 3,4-dichlorophenol, 2-fluorophenol, 3-fluorophenol, 4-fluorophenol, 3-methyl-4-nitrophenol, 3-isopropyl-4-nitrophenol, 3-isopropyl-4-nitrophenol, 2-nitroanisole, 4-nitropyrocatechol, 2-nitrophenol, 3-nitrophenol, 2-methoxy-3-methylphenol, 2-methoxy-4-methylphenol, 2-methoxyphenol, 3-methoxyphenol and 4-methoxyphenol. Preferred alcohols of the formula $HOR^1$ are 2-isopropylphenol, 2,6-di-tert-butyl-4-methylphenol, 2,4-di-tert-butylphenol, 2,6-di-tert-butylphenol, phenol, 2-fluorophenol, 3-fluorophenol, 4-fluorophenol, 4-nitropyrocatechol, 2-methoxy-4-methylphenol, 2-trifluoromethylphenol, 3,5-bis(trifluoromethyl)phenol, 4-cyanophenol, etc.

Suitable alcohols of the formula HO—A—OH, where A has the abovementioned meanings, are known. These include, for example, biphenyl-2,2'-diol and binaphthyl-2,2'-diol. Further suitable diols are mentioned in U.S. Pat. No. 5,312,996, column 19, which is hereby expressly incorporated by reference.

Both the reaction of the compound (III) with (IV) to give (V) and the further reaction to give the bidentate phosphonite ligands of the formula (I) take place in general at elevated temperatures of from about 40 to about 200° C. Both reactions can be carried out in the presence of a base, for example an aliphatic amine, such as diethylamine, propylamine, dibutylamine, trimethylamine, tripropylamine or preferably triethylamine or pyridine. The elimination of hydrogen halide is preferably effected purely thermally in the first reaction step.

Advantageously, the preparation of the phosphonite ligands of the formula I which are used according to the invention is effected without using organomagnesium or organolithium compounds. The simple reaction sequence permits a wide variation of the ligands. The preparation is thus carried out efficiently and economically from readily available starting materials.

For the preparation of the novel catalysts, at least one phosphonite ligand of the formula I can be reacted with a metal of subgroup VIII, e.g. nickel, or with a compound of the metal in the presence of a reducing agent or a complex of the metal, in each case in an inert solvent. Suitable nickel compounds of, for example, compounds in which the transition metal assumes an oxidation state higher than 0 and which are reduced in situ during the reaction with the phosphonite ligand of the formula I, in the presence or absence of a suitable reducing agent. These include, for example, the halides, preferably the chlorides, and the acetates of the abovementioned transition metals. $NiCl_2$ is preferably used. Suitable reducing agents are, for example, metals, preferably alkali metals, such as Na and K, aluminum, zinc and trialkylaluminum compounds.

If complex compounds of the transition metal are themselves used for the preparation of the phosphonite-nickel(0) complexes, the transition metal is preferably already in the zero-valent state in said complex compounds. Preferably, complexes having ligands which correspond to the abovementioned, additional ligands of the novel complexes are used for the preparation. In this case, the preparation is carried out by partial or complete ligand exchange with the phosphonite ligands of the formula (I) which are described above.

The nickel complex bis(1,5-cyclooctadienyl)nickel(0) is preferred.

Suitable inert solvents for the preparation of the nickel(0) complexes are, for example, aromatics, such as benzene, toluene, ethylbenzene and chlorobenzene, ethers, preferably diethyl ether and tetrahydrofuran, and haloalkanes, for example dichloromethane, chloroform, dichloroethane and trichloroethane. Other suitable solvents are the liquid starting materials and/or products of the catalyzed reaction. The temperature is from −70 to 150° C., preferably from 0° C. to 100° C., particularly preferably about room temperature.

If elemental nickel is used for the preparation of the phosphonite-nickel(0) complexes, it is preferably in the form of a powder. The reaction of nickel and phosphonite ligand is preferably effected in a product of the catalyzed reaction, such as the hydrocyanation reaction, as the solvent, for example in a mixture of monoolefinic $C_5$-mononitriles or, preferably, in 3-pentenenitrile or 2-methyl-3-butenenitrile. If required, the ligand may also be used as solvent. The temperature is from about 0 to 150° C., preferably 60 to 100° C.

The molar ratio of metal of subgroup VIII to bidentate phosphonite ligand is preferably from about 1:1 to 1:5, particularly preferably from 1:1 to 1:3.

The present invention furthermore relates to a process for the preparation of mixtures of monoolefinic $C_5$-mononitriles having a nonconjugated C=C and C≡N bond by catalytic hydrocyanation of butadiene or of a 1,3-butadiene-containing hydrocarbon mixture, wherein the hydrocyanation is carried out in the presence of at least one of the novel catalysts described above.

For the preparation of mixtures of monoolefinic $C_5$-mononitriles which contain, for example, 3-pentenenitrile and 2-methyl-3-butenenitrile and which are suitable as intermediates for further processing to give adipodinitrile, pure butadiene or 1,3-butadiene-containing hydrocarbon mixtures may be used.

If a hydrocarbon mixture is used in the novel process, said mixture has a 1,3-butadiene content of at least 10, preferably at least 25, in particular at least 40, % by volume.

1,3-Butadiene-containing hydrocarbon mixtures are available on an industrial scale. Thus, a hydrocarbon mixture referred to as a $C_4$ cut and having a high total olefin fraction is obtained, for example, in the working-up of mineral oil by steam cracking of naphtha, about 40% of said fraction being accounted for by 1,3-butadiene and the remainder by monoolefins and polyunsaturated hydrocarbons as well as alkanes. These streams always also contain small amounts of in general up to 5% of alkynes, 1,2-dienes and vinylacetylene.

Pure 1,3-butadiene can be isolated from industrially available hydrocarbon mixtures, for example by extractive distillation.

$C_4$ cuts are, if required, essentially freed from 1,2-dienes, such as propadiene, and from alkenynes, e.g. vinylacetylene, before the hydrocyanation of alkynes, such as propyne or butyne. Otherwise, products may be obtained in which a C=C double bond is present in conjugation with the C≡N bond. These may act as catalyst poisons for the first reaction step of the adipic acid preparation, the monoaddition reaction of hydrogen cyanide.

If required, those components which may give rise to catalyst poisons, in particular alkynes, 1,2-dienes and mixtures thereof, are therefore partially or completely removed from the hydrocarbon mixture. To remove these components, the $C_4$ cut is subjected to a partial catalytic hydrogenation before the addition reaction with hydrogen cyanide. This partial hydrogenation is effected in the presence of a hydrogenation catalyst which is capable of hydrogenating alkynes and 1,2-dienes selectively alongside other dienes and monoolefins.

Suitable heterogeneous catalyst systems for the selective hydrogenation are known and comprise in general a transition metal compound on an inert support. They are in particular those described in U.S. Pat. Nos. 4,587,369, 4,704,492 and 4,493,906, which are hereby fully incorporated by reference. Further suitable catalyst systems based on copper are sold by Dow Chemical as KLP catalyst.

The addition reaction of hydrogen cyanide with 1,3-butadiene or with 1,3-butadiene-containing hydrocarbon mixture, for example a pretreated, partially hydrogenated $C_4$ cut, can be carried out continuously, semicontinuously or batchwise.

Suitable reactors for the reaction are known to a person skilled in the art and are described, for example, in Ullmanns Enzyklopädie der technischen Chemie, Vol. 1, 3rd edition, 1951, page 743 et seq. and page 769 et seq. Preferably, a stirred catalyst cascade or a tube reactor is used for a continuous process.

If the addition reaction of the hydrogen cyanide with 1,3-butadiene or with a 1,3-butadiene-containing hydrocarbon mixture is carried out semicontinuously or batchwise, for example, an autoclave which, if desired, can be provided with a stirring apparatus and an internal lining is used for the novel process.

A suitable semicontinuous process comprises:

a) Filling a reactor with 1,3-butadiene or with the hydrocarbon mixture, if required, a part of the hydrogen cyanide and a novel hydrocyanation catalyst which may have been produced in situ and, if required, a solvent. Suitable solvents are those mentioned above for the preparation of the novel catalysts, preferably aromatic hydrocarbons, such as toluene or xylene, or tetrahydrofuran.

b) Reaction of the mixture at elevated temperatures and superatmospheric pressure. The reaction temperature is in general from about 0 to 200° C., preferably from about 50 to 150° C. The pressure is in general from about 1 to 200 bar, preferably from about 1 to 100, in particular from 1 to 50, particularly preferably from 1 to 20, bar. During the reaction, hydrogen cyanide is fed in at the rate at which it is consumed.

c) If required, completion of the reaction by continued reaction and subsequent working up. To complete the reaction, the reaction time may be followed by a subsequent reaction time of from 0 minutes to about 5 hours, preferably from about 1 hour to 3.5 hours, in which hydrogen cyanide is no longer fed into the autoclaves. The temperature is left essentially constant at the previously set reaction temperature during this time. Working up is effected by conventional methods and comprises the removal of the unconverted 1,3-butadiene and of the unconverted hydrogen cyanide, for example by washing or extraction, and working-up of the remaining reaction mixture by distillation to isolate the desired products and recover the still active catalyst.

In a further suitable variant of the novel process, the addition reaction of the hydrogen cyanide with the 1,3-butadiene-containing hydrocarbon mixture is carried out batchwise. Essentially the reaction conditions described in the semicontinuous process are maintained, no additional hydrogen cyanide being fed in in step b) but hydrogen cyanide being completely initially taken.

The addition reaction of the hydrogen cyanide with 1,3-butadiene or a 1,3-butadiene-containing hydrocarbon mixture is preferably carried out continuously. The reaction is generally carried out so that essentially no relatively large amounts of unconverted hydrogen cyanide are present in the reactor. Suitable processes for the continuous hydrocyanation are known to a person skilled in the art. They include, for example, a feed process in which 1,3-butadiene and hydrocyanic acid are fed to a reactor via separate feeds at the rate at which they are consumed. The catalysts can be fed in together with one of the starting materials or via a separate feed. Suitable, preferably thoroughly mixable reactors are likewise known to a person skilled in the art. They include, for example, stirred catalysts, catalytic cascades and tube reactors, which, if required, are provided with an internal lining. The working-up of the reaction products, too, is preferably carried out by a conventional continuous method.

In general, the 3-pentenenitrile/2-methyl-3-butenenitrile ratio obtained in the monoaddition reaction of hydrogen cyanide with 1,3-butadiene or the 1,3-butadiene-containing hydrocarbon mixture immediately after the end of the addition reaction (unconverted hydrogen cyanide no longer present) is at least 0.4:1. Advantageously, an isomerization additionally takes place at higher reaction temperatures and/or during longer reaction times in the presence of the novel catalysts, the 3-pentenenitrile/2-methyl-3-butenenitrile ratio obtained then generally being about 2:1, preferably about 5:1, in particular about 8:1.

In general, the preparation of adipodinitrile from butadiene or from a butadiene-containing hydrocarbon mixture by addition of 2 molar equivalents of hydrogen cyanide can be divided into three steps:

1. Preparation of $C_5$-monoolefin mixtures having a nitrile function.
2. Isomerization of the 2-methyl-3-butenenitrile contained in these mixtures to give 3-pentenenitrile and isomerization of the 3-pentenenitrile thus formed and of the 3-pentenenitrile already contained from step 1 to give various n-pentenenitriles. A very high fraction of 3-pentenenitrile or 4-pentenenitrile and a very small fraction of conjugated 2-pentenenitrile and 2-methyl-2-butenenitrile which may act as a catalyst poison should be formed.
3. Preparation of adipodinitrile by an addition reaction of hydrogen cyanide with the 3-pentenenitrile formed in step 2 and isomerized beforehand "in situ" to 4-pentenenitrile.

The novel catalysts based on phosphonite ligands are also advantageous for the positional and double bond isomerization in step 2 and/or the addition reaction of the second molecule of hydrogen cyanide in step 3.

The present invention therefore relates to a process for the catalytic isomerization of branched aliphatic monoalkenenitriles having a nonconjugated C=C and C≡N bond to give linear monoalkenenitriles, wherein the isomerization is carried out in the presence of a novel catalyst.

Suitable branched aliphatic monoalkenenitriles are preferably acyclic, aliphatic, nonconjugated 2-alkyl-3-monoalkenenitriles and in particular 2-methyl-3-butenenitrile. Mixtures of monoolefinic $C_5$-mononitriles, as obtainable by the process, described above, for the catalytic hydrocyanation of butadiene or of 1,3-butadiene-containing hydrocarbon mixtures, are preferably used for the isomerization. Advantageously, the novel catalysts exhibit good activity with respect to the formation of linear monoalkene nitrites. The isomerization can, if desired, be effected in the presence of a conventional promoter, for example a Lewis acid, such as $AlCl_3$ or $ZnCl_2$. Advantagously, the novel catalysts generally permit isomerization without the addition of a promoter. The selectivity of the novel catalysts in the isomerization without the addition of a promoter is in general higher than that with the addition of a promoter. Furthermore, expensive removal of the promoter of the isomerization can be dispensed with. Thus, in principle only one catalyst circulation for hydrocyanation, isomerization and, if required, an addition reaction of a second molecule of hydrogen cyanide is required. Dispensing with the promoter and simplification of the process which is possible in principle generally permit a reduction of the costs compared with known processes.

The temperature in the isomerization is from about 50 to 160° C., preferably from 70 to 130° C.

The present invention furthermore relates to a process for the preparation of adipodinitrile by catalytic hydrocyanation of linear monoolefinic $C_5$-mononitriles, wherein the hydrocyanation is carried out in the presence of a novel catalyst. Advantageously, a mixture of monoolefinic $C_5$-mononitriles which is obtainable by the novel process for the catalytic hydrocyanation of butadiene or of a 1,3-butadiene-containing hydrocarbon mixture and which, if required, was additionally subjected to working up and/or to isomerization by the novel isomerization process described above is used for the hydrocyanation. In a suitable embodiment of the novel process, the hydrocyanation of the monoolefinic $C_5$-mononitriles is carried out in the presence of a promoter, for example a Lewis acid, such as $AlCl_3$, $ZnCl_2$, $BF_3$, $B(C_6H_5)_3$, $SnCl_4$, $Sn(C_6H_5)_3OSO_2CF_3$, etc.

In a suitable embodiment of the novel process for the preparation of adipodinitrile, the catalytic hydrocyanation of butadiene or of a 1,3-butadiene-containing hydrocarbon mixture (Step 1) and the isomerization (Step 2) are carried out in the manner of a one-pot reaction without isolation of the hydrocyanation products. Hydrocyanation and isomerization can be carried out, for example, in one reactor, the reaction temperature being increased, if required, after the end of the hydrogen cyanide addition. Hydrocyanation and isomerization can also be carried out in separate reactors, where, for example, after the end of the monoaddition reaction of hydrogen cyanide in a first reactor, the catalyst-containing reaction mixture is transferred, without isolation and working up, to a second reactor and is isomerized therein.

In a further suitable embodiment of the novel process, all three steps of the adipodinitrile preparation, i.e. preparation of monoolefinic $C_5$-mononitriles, isomerization and addition of the second molecule of hydrogen cyanide, are carried out in the manner of a one-pot reaction.

The present invention therefore relates to a process for the preparation of adipodinitrile, comprising a) preparation of a mixture of monoolefinic $C_5$-mononitriles having a nonconjugated C=C and C≡N bond by catalytic hydrocyanation of butadiene or of a 1,3-butadiene-containing hydrocarbon mixture,
b) catalytic isomerization of the mixture from a), and
c) catalytic hydrocyanation of the isomerized mixture from b), wherein the steps a), b) and c) are carried out in the presence of at least one novel catalyst and without isolation of the product or products from step a) and/or b).

The novel catalysts can be prepared simply and thus economically from readily obtainable intermediates, some of which are commercially available. Advantageously, they have high activity and good selectivity with respect to the monoadducts or isomerization products obtained in the hydrocynation of 1,3-butadiene-containing hydrocarbon mixtures. In general, they have higher stability relative to hydrogen cyanide than conventional hydrocyanation catalysts and, in the hydrocyanation, an excess of hydrogen cyanide can also be added to said catalysts without resulting in marked deposition of inactive nickel(II) compounds, e.g. nickel(II) cyanide. In contrast to known hydrocyanation catalysts based on non-complex phosphine and phosphite ligands, the novel catalysts are therefore suitable not only for continuous hydrocyanation processes in which an excess of hydrogen cyanide in the reaction mixture can generally be effectively avoided but also for semicontinuous processes and batch processes in which a large excess of hydrogen cyanide is generally present. Thus, the catalysts used according to the invention and the hydrocyanation processes based on them generally have higher catalyst recycling rates and longer catalyst on-stream times than known processes. This is advantageous not only for achieving better cost-efficiency but also from ecological points of view, since the nickel cyanide formed from the active catalyst with hydrogen cyanide is highly toxic and must be worked up or disposed of at high cost. Moreover, in the preparation of the novel catalysts, generally no excess or a smaller excess of ligand is required relative to the metal of subgroup VIII than in the case of conventional catalysts.

In addition to the hydrocyanation of 1,3-butadiene-containing hydrocarbon mixtures, the catalysts of the formula I are generally suitable for all conventional hydrocyanation processes. In particular, the hydrocyanation of nonactivated olefins, for example of styrene and 3-pentenenitrile, may be mentioned.

The catalysts which are described above and comprise chiral phosphonite ligands of the formula I are suitable for enantioselective hydrocyanation.

The nonrestricting examples which follow illustrate the invention.

EXAMPLES

The following ligand I was used in Examples 1 and 3 and the ligand II was used in Examples 2 and 4:

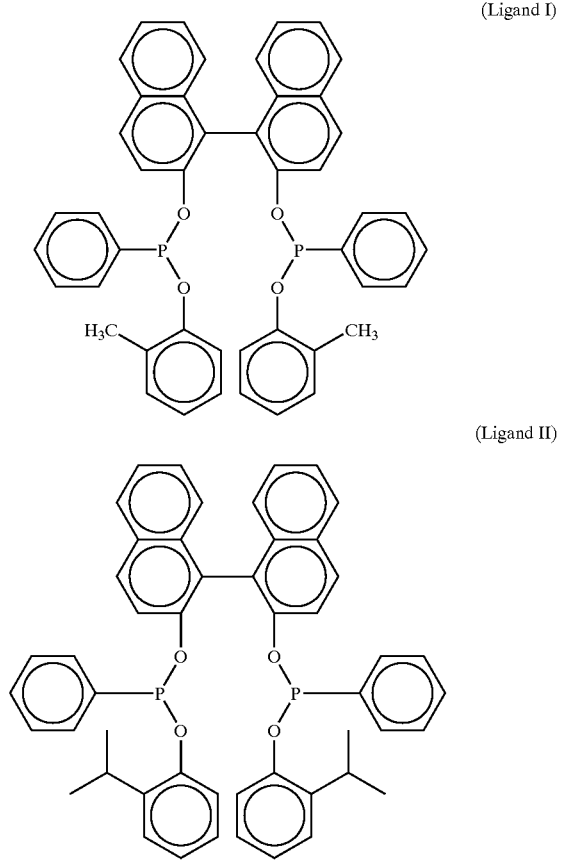

(Ligand I)

(Ligand II)

Example 1
(According to the Invention)
Semicontinuous Hydrocyanation of 1,3-butadiene 0.41 g (1.5 mmol) of bis(1,5-cyclooctadienyl)nickel(0), 2.14 g of ligand I and 10 ml of toluene are initially taken under argon at room temperature in a glass autoclave and stirred for 10 minutes, the reaction batch acquiring a red-brown color. A mixutre of 7.9 g (146 mmol) of 1,3-butadiene and 40 g of toluene is then added. The glass autoclave is tightly closed and the reaction mixture is heated to 70° C., an initial pressure of 1.2 bar being established. A mixture of 3.2 g (118 mmol) of freshly distilled hydrocyanic acid in 40 g of toluene is continuously metered in over a period of 90 minutes. Thereafter, the pressure has fallen to 0.5 bar. The reaction is then completed in the course of a further 120 minutes at about 70° C. Toluene is used for washing the reaction discharge. The course of the reaction is monitored by pressure and temperature measurement.

In a subsequent Volhard cyanide determination, hydrogen cyanide conversion of more than 99% is determined.

GC analysis (column: 30 m Stabil-Wachs, temperature program: 5 minutes isothermally at 50° C., then heating up at a rate of 5° C./min at 240° C., gas chromatograph: Hewlett Packard HP 5890) with internal standard (benzonitrile): 99.4% of 3-pentenenitrile, 4-pentenenitrile and 2-methyl-3-butenenitrile, based on hydrogen cyanide used.

3-Pentenenitrile: 2-methyl-3-butenenitrile ratio=0.41:1

As shown in the following Example 2, the ratio of 3-pentenenitrile to 2-methyl-3-butenenitrile is shifted in favor of 3-pentenenitrile by prolonging the reaction time beyond the end of the hydrogen cyanide addition. The addition of a promoter is not necessary.

Example 2
(According to the Invention)
Semicontinuous Hydrocyanation of 1,3-butadiene with Isomerization 0.41 g (1.5 mmol) of bis(1,5-cyclooctadienyl)nickel(0), 2.9 g of ligand II and 10 g of toluene are initially taken under an argon atmosphere at room temperature in a glass autoclave and stirred for 10 minutes, the reaction batch acquiring a red-brown color. A mixture of 8.1 g (150 mmol) of 1,3-butadiene and 40 g of toluene is then added. The glass autoclave is tightly closed and the reaction mixture is heated to 90° C. A mixture of 4.0 g of freshly distilled hydrocyanic acid in 40 g of toluene is metered in continuously over a period of 90 minutes. After the end of the addition, the temperature is increased to 110° C. The course of the isomerization (ratio of 3-pentenenitrile to 2-methyl-3-butenenitrile) is investigated at regular intervals (0, 3, 6, 22 h) by means of GC analysis, as described in Example 1. The results are shown in Table 1.

TABLE 1

| Time after end of addition [h] | 3-Pentenenitrile: 2-methyl-3-butenenitrile ratio |
| --- | --- |
| 0 | 0.27:1 |
| 3 | 1.94:1 |
| 6 | 4.75:1 |
| 22 | 8.25:1 |

Since, owing to the taking of samples for gas chromatography, an exact determination of the yield was not possible, the same batch was run again without sampling. There was no subsequent reaction time.

Yield: 99.6%

3-Pentenenitrile: 2-methyl-3-butenenitrile ratio=0.22:1 (Determination of yield: see Example 1)

Example 3

(According to the Invention)

Isomerization of 2-methyl-3-butenenitrile to 3-pentenenitrile 0.72 g of ligand I, 15 ml of toluene and 0.14 g (0.5 mmol) of bis(1,5-cyclooctadienyl)nickel(0) are initially taken under an argon atmosphere and stirred at room temperature for 45 minutes. The catalyst complex which forms is precipitated from the initially homogeneous solution. The volatile components are removed at highly superatmospheric pressure. 40.5 g (500 mmol) of 2-methyl-3-butenenitrile are added to the remaining solid. The solution is heated to 110° C. The course of the reaction is investigated at regular intervals by means of a gas chromatograph. The product ratio after a reaction time of 300 minutes is shown in Table 2. All products and by-products shown there were assigned beforehand by means of gas chromatography, GC-MS, GC-MS-IR and NMR. All values are in GC percent by area.

Weight of sample: 1.0160 g
Weight of standard: 1.4416 g

TABLE 2

Product ratio after a reaction time of 300 minutes

| Compound | Amount [GC % by area] |
| --- | --- |
| trans-2-methyl-2-butenenitrile | 0.98 |
| 2-methyl-3-butenenitrile | 7.41 |
| trans-2-pentenenitrile | 0 |
| cis-2-methyl-2-butenenitrile | 0.21 |
| 4-pentenenitrile | 0.33 |
| trans-3-pentenenitrile | 43.10 |
| cis-3-pentenenitrile | 1.32 |
| methylglutaronitrile | 0.14 |
| benzonitrile (standard) | 45.55 |

Conversion: 71.65%
Selectivity: >99% (Note: The starting material itself contains about 1% of cis- and trans-2-methyl-2-butenenitrile)

As demonstrated by Example 3, isomerization using the novel catalysts is also possible without the addition of a promoter.

Example 4

(According to the Invention)

An Isomerization of 2-methyl-3-butenenitrile to 3-pentenenitrile 0.39 g of ligand II, 8 ml of toluene and 0.07 g (0.25 mmol) of bis(1,5-cyclooctadienyl)nickel(0) are initially taken under an argon atmosphere and stirred at room temperature for 30 minutes. Some of the catalyst complex which forms is precipitated from the initially red homogeneous solution. The volatile components are removed at highly superatmospheric pressure. 20.2 g (250 mmol) of 2-methyl-3-butenenitrile are added to the remaining solid. The solution is heated to 125° C. The course of the reaction is investigated at regular intervals by means of a gas chromatograph. The product ratio after a reaction time of 300 minutes is shown in Table 3. All products and by-products shown there were assigned beforehand by means of gas chromatography, GC-MS, GC-MS-IR and NMR. All values are in GC percent by area.

Weight of sample: 1.2109 g
Weight of standard: 1.00262 g

TABLE 3

Product ratio after a reaction time of 300 minutes

| Compound | Amount [GC % by area] |
| --- | --- |
| trans-2-methyl-2-butenenitrile | 3.87 |
| 2-methyl-3-butenenitrile | 2.16 |
| trans-2-pentenenitrile | 0.36 |
| cis-2-methyl-2-butenenitrile | 1.43 |
| 4-pentenenitrile | 1.31 |
| trans-3-pentenenitrile | 38.20 |
| cis-3-pentenenitrile | 3.60 |
| methylglutaronitrile | 0 |
| benzonitrile (standard) | 47.95 |

Conversion: 95.74%

We claim:

1. A catalyst composition comprising a complex of a metal of group VIII, and a bidentate phosphonite ligand of the formula I

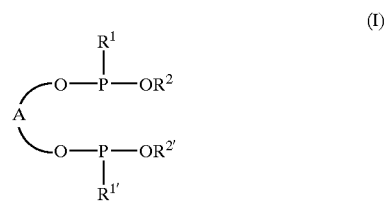

where

A is a $C_2$- to $C_7$-alkylene bridge which may have 1, 2 or 3 double bonds and/or 1, 2 or 3 substituents which are selected from alkyl, cycloalkyl and aryl, it being possible for the aryl substituent additionally to carry 1, 2 or 3 substituents which are selected from alkyl, alkoxy, halogen, trifluoromethyl, nitro, alkoxycarbonyl and cyano, and/or the $C_2$- to $C_7$-alkylene bridge may be interrupted by 1, 2 or 3 non-neighboring, unsubstituted or substituted heteroatoms, and/or the $C_2$- to $C_7$-alkylene bridge may be fused with one, two or three aryl and/or hetaryl groups, it being possible for the fused aryl and hetaryl groups each to carry 1, 2 or 3 substituents which are selected from alkyl, cycloalkyl, aryl, alkoxy, cycloalkoxy, aryloxy, acyl, halogen, trifluoromethyl, nitro, cyano, carboxyl, alkoxycarbonyl and $NE^1E^2$, where $E^1$ and $E^2$ are identical or different and are each alkyl, cycloalkyl or aryl, $R^1$ and $R^{1'}$, independently of one another, are each alkyl, cycloalkyl, aryl or hetaryl, each of which may carry 1, 2 or 3 substituents which are selected from alkyl, cycloalkyl and aryl, $R^2$ and $R^{2'}$, independently of one another, are each alkyl, cycloalkyl, aryl or hetaryl, it being possible for the aryl and hetaryl groups each to carry 1, 2 or 3 substituents which are selected from alkyl, cycloalkyl, aryl, alkoxy, cycloalkoxy, aryloxy, acyl, halogen trifluoromethyl, nitro, cyano, carboxyl, alkoxycarbonyl and $NE^1E^2$, where $E^1$ and $E^2$ may have the abovementioned meanings, or a salt or mixture thereof.

2. The catalyst composition as claimed in claim 1, A being a radical of the formulae II.1 to II-5

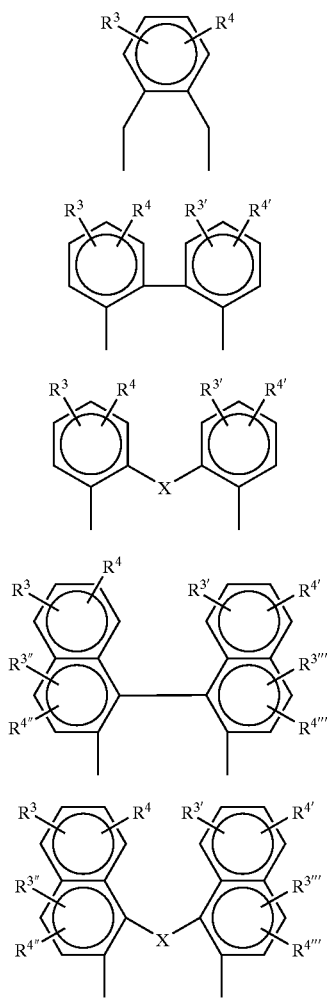

(II.1)

(II.2)

(II.3)

(II.4)

(II.5)

where

X is O, S or NR⁵, where
R⁵ is alkyl, cycloalkyl or aryl,
or X is a $C_1$- to $C_3$-alkylene bridge which may have a double bond and/or an alkyl, cycloalkyl or aryl substituent, wherein the aryl is optionally substituted by one, two or three substituents, which are selected from alkyl, alkoxy, halogen, trifluoromethyl, nitro, alkoxycarbonyl and cyano,
or X is a $C_2$- or $C_3$-alkylene bridge which is interrupted by O, S or NR⁵,
and R³, R³', R³'', R³''', R⁴, R⁴', R⁴'' and R⁴''' independently of one another, are each hydrogen, alkyl, alkoxy, halogen, trifluoromethyl, nitro, alkoxycarbonyl or cyano.

3. The catalyst composition as claimed in claim 1, R¹ and R¹', independently of one another, being alkyl or aryl.

4. The catalyst composition as claimed in claim 1, R² and R²', independently of one another, each being phenyl substituents which may have one or two substituents which are selected from alkyl, alkoxy, halogen, trifluoromethyl, nitro, cyano, alkoxycarbonyl and carboxyl.

5. The catalyst composition as claimed in claim 1, the phosphonite ligand of the formula I being selected from ligands of the formulae Ia to Ic

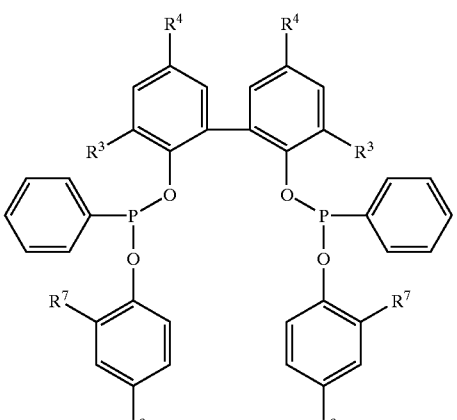

(Ia)

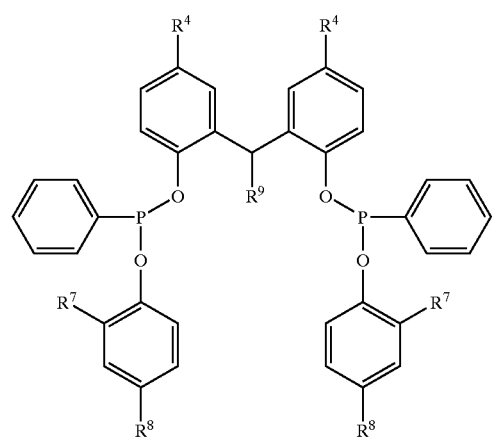

(Ib)

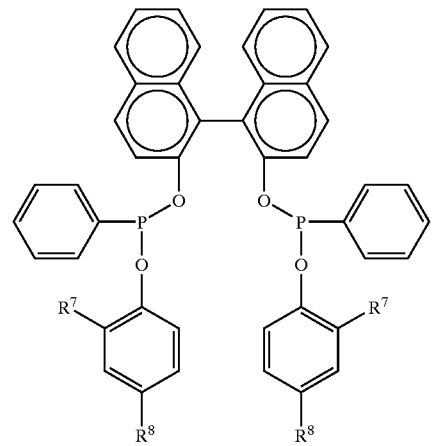

(Ic)

where, in the formula Ia, R³, R⁴, R⁷ and R⁸ have the following meanings:

| R³ | R⁴ | R⁷ | R⁸ |
|---|---|---|---|
| H | H | H | H |
| tert-butyl | methyl | H | H |
| tert-butyl | methoxy | H | H |
| H | H | methyl | H |
| H | H | ethyl | H |
| H | H | isopropyl | H |
| H | H | tert-butyl | H |

-continued

| $R^3$ | $R^4$ | $R^7$ | $R^8$ |
|---|---|---|---|
| H | Cl | H | H |
| H | $CF_3$ | H | H |
| H | H | methyl | methoxy | in the formula Ib, $R^4$, $R^7$, $R^8$ and $R^9$ have the following meanings

| $R^4$ | $R^7$ | $R^8$ | $R^9$ |
|---|---|---|---|
| H | H | H | H |
| Cl | H | H | H |
| methoxy | H | H | H |
| H | H | H | phenyl |
| H | methyl | H | H |
| H | methyl | methoxy | H |
| H | methyl | methoxy | phenyl | in the formula Ic, $R^7$ and $R^8$ have the following meanings:

| $R^7$ | $R^8$ |
|---|---|
| H | H |
| methyl | H |
| ethyl | H |
| isopropyl | H |
| tert-butyl | H |
| methyl | methoxy |
| i-propyl | H |
| i-propyl | methoxy |
| H | Cl |
| H | $CF_3$ |

6. The catalyst composition as claimed in claim 1, which additionally has at least one further ligand selected from cyanide, halides, amines, carboxylates, acetylacetone, arylsulfonates, alkanesulfonates, hydride, CO, olefins, dienes, cycloolefins, nitriles, N-containing heterocycles, aromatics and heteroaromatics, ethers, $PF_3$ and mono-, bi- and polydentate phosphine, phosphinite and phosphite ligands.

7. The catalyst composition as claimed in claim 1, the metal of group VIII being cobalt, rhodium, ruthenium, palladium or nickel.

8. A phosphonite ligand of the formula I

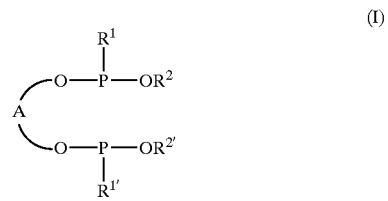

as defined in claim 1, where
$R^2$ and $R^{2'}$, independently of one another, are each alkyl, cycloalkyl, aryl or hetaryl, it being possible for the aryl and hetaryl groups each to carry one or two substituents which are selected from alkyl, cycloalkyl, aryl, alkoxy, cycloalkoxy, aryloxy, acyl, halogen, trifluoromethyl, nitro, cyano, carboxyl, alkoxycarbonyl and $NE^1E^2$, where $E^1$ and $E^2$ are idendical or different and are each alkyl, cycloalkyl or aryl.

9. A process for the preparation of a mixture of monoolefinic $C_5$-mononitriles having a nonconjugated C=C and C≡N bond by catalytic hydrocyanation of butadiene or of a 1,3-butadiene-containing hydrocarbon mixture, wherein the hydrocyanation is carried out in the presence of a catalyst composition as claimed in claim 1.

10. A process for the catalytic isomerization of branched aliphatic monoalkenenitriles having a nonconjugated C=C and C≡N bond to give linear monoalkenenitriles, wherein the isomerization is carried out in the presence of a catalyst composition as claimed in claim 1.

11. A process for the preparation of adipodinitrile by catalytic hydrocyanation of a linear monoolefinic $C_5$-mononitrile, wherein the hydrocyanation is carried out in the presence of a catalyst composition as claimed in claim 1.

12. A process for the preparation of adipodinitrile, comprising
a) preparation of a mixture of monoolefinic $C_5$-mononitriles having a nonconjugated C=C and C≡N bond by catalytic hydrocyanation of butadiene or of a 1,3-butadiene- containing hydrocarbon mixture,
b) catalytic isomerization of the mixture from a), and
c) catalytic hydrocyanation of the isomerized mixture from b), wherein the steps a), b) and c) are carried out in the presence of at least one catalyst composition as claimed in claim 1 and without isolation of the product or products from step a) and/or b).

13. A process for the hydrocyanation and/or positional and double-bond isomerization of olefins, wherein the hydrocyanation and/or positional and double-bond isomerization of olefins is carried out in the presence of a catalyst composition as claimed in claim 1.

14. The catalyst composition as claimed in claim 3, wherein $R^1$ and $R^{1'}$, independently of one another, are selected from the group consisting of phenyl, 1-naphthyl and 2-naphthyl.

* * * * *